United States Patent [19]

Brunavs et al.

[11] Patent Number: 5,622,987
[45] Date of Patent: Apr. 22, 1997

[54] 5,6-DIHYDRONAPHTHO [1,2-B]PYRANS AND THEIR USE AS PHARMACEUTICAL COMPOUNDS

[75] Inventors: Michael Brunavs, Frimley; Colin P. Dell, Dorking; Peter T. Gallagher, Camberley; William M. Owton, Lightwater; Colin W. Smith, Bracknell, all of United Kingdom

[73] Assignees: Eli Lilly and Company, Indianapolis, Ind.; Lilly Industries Limited, Basingstoke, England

[21] Appl. No.: 461,342

[22] Filed: Jun. 5, 1995

Related U.S. Application Data

[62] Division of Ser. No. 293,786, Aug. 22, 1994, which is a division of Ser. No. 14,016, Feb. 5, 1993, Pat. No. 5,378,699.

[30] Foreign Application Priority Data

Feb. 19, 1992 [GB] United Kingdom .................. 9203497

[51] Int. Cl.⁶ .................................................. A61K 31/35
[52] U.S. Cl. .................... 514/454; 549/389; 514/277; 514/438; 514/443; 514/456; 514/461; 514/464; 514/212; 514/408; 514/210
[58] Field of Search ............................ 549/389; 514/454, 514/277, 438, 443, 456, 461, 464, 212, 408, 210

[56] References Cited

U.S. PATENT DOCUMENTS 5,284,868  2/1994  Dell et al. ........................... 514/454

OTHER PUBLICATIONS

Elnagdi, et al., *Naturfoschung B*, 47(4), pp. 572–578 (1992).
Elagamey, et al. *Indian Journal of Chemistry*, 29B, 885–886 (1990).
Elagamey, et al., *Collection Czechoslovak Chem. Commun.*, 53(7), 1534–1538 (1988).
Otto, et al., *Monatshefte für Chemi*, 110, 115–119 (1979).
Otto, et al., *Monatshefte für Chemi*, 110. 249–256 (1979).
Otto, et al., *Arch. Pharm.*, 312(6), 548–550 (1979).
Maybridge Chemical Company, Structure List No. 183, May 1989.
Maybridge Chemical Company, Exclusive Listing No. 1187/513684/13279, Nov. 6, 1987.
Maybridge Chemical Company, Exclusive Listing No. 288/51345/13684, Feb. 19, 1988.

*Primary Examiner*—Charles T. Jordan
*Assistant Examiner*—John R. Hardee
*Attorney, Agent, or Firm*—James P. Leeds; Janelle D. Strode

[57] ABSTRACT

Pharmaceutical compounds of the formula

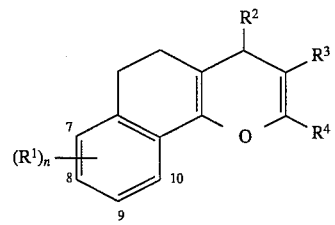

in which
n is 0, 1 or 2 and $R^1$ is attached at any of the positions 7, 8, 9 or 10, and each $R^1$ is halo, carboxy, trifluoromethyl, hydroxy, $C_{1-4}$ alkyl, $C_{1-4}$ alkoxy, $C_{1-4}$ alkylthio, hydroxy-$C_{1-4}$ alkyl, hydroxy-$C_{1-4}$ alkoxy, nitrogen-containing heterocyclyl, nitro, trifluoromethoxy, —$COOR^5$ where $R^5$ is an alkyl group, —$COR^6$, —$CONR^6R^7$ or —$NR^6R^7$ where $R^6$ and $R^7$ are each hydrogen or $C_{1-4}$ alkyl;

$R^2$ is phenyl, naphthyl or heteroaryl selected from thienyl, pyridyl, benzothienyl, quinolinyl, benzofuranyl or benzimidazolyl, said phenyl, naphthyl and heteroaryl groups being optionally substituted, or $R^2$ is furanyl optionally substituted with $C_{1-4}$ alkyl;

$R^3$ is nitrile, carboxy, —$COOR^8$ where $R^8$ is an alkyl group, or —$CONR^9R^{10}$ where $R^9$ and $R^{10}$ are each hydrogen or $C_{1-4}$ alkyl; and $R^4$ is —$NR^{11}R^{12}$, —$NR^{11}COR^{12}$, —$N(COR^{11})_2$ or —$N=CHOCH_2R^{11}$ where $R^{11}$ and $R^{12}$ are each hydrogen or $C_{1-4}$ alkyl optionally substituted with carboxy, —$N=CH-NR^{13}R^{14}$ where $R^{13}$ is hydrogen or $C_{1-4}$ alkyl and $R^{14}$ is $C_{1-4}$ alkyl, optionally substituted phenyl or optionally substituted heteroaryl,

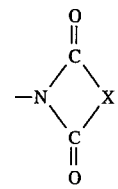

where X is $C_{2-4}$ alkylene, or —$NHSO_2R^{15}$ where $R^{15}$ is $C_{1-4}$ alkyl, trifluoromethyl or optionally substituted phenyl; and salts thereof.

6 Claims, No Drawings

5,6-DIHYDRONAPHTHO [1,2-B]PYRANS AND THEIR USE AS PHARMACEUTICAL COMPOUNDS

This application is a division of application Ser. No. 08/293,786, filed Aug. 22, 1994, which is a division of application Ser. No. 08/014,016, filed Feb. 5, 1993, now U.S. Pat. No. 5,378,699.

This invention relates to pharmaceutical compounds, their preparation and use.

The synthesis of certain phenyl-substituted 5,6-dihydronaphtho [1,2-b]pyrans is described by Otto H-H. et al. in Monatshefte für Chemie 110, 115–119 and 249–256 (1979), and Arch. Pharm. (Weinheim Ger.), 312(6), 548–550 (1979). No biological properties are ascribed to the compounds disclosed.

The present invention relates to compounds of the formula (I):

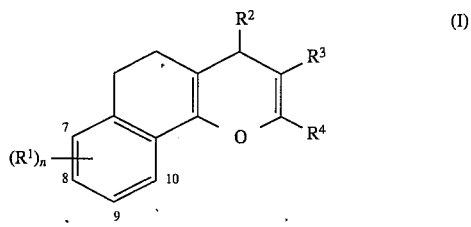

in which n is 0, 1 or 2 and $R^1$ is attached at any of the positions 7, 8, 9 or 10, and each $R^1$ is halo, carboxy, trifluoromethyl, hydroxy, $C_{1-4}$ alkyl, $C_{1-4}$ alkoxy, $C_{1-4}$ alkylthio, hydroxy-$C_{1-4}$ alkyl, hydroxy-$C_{1-4}$ alkoxy, nitrogen-containing heterocyclyl, nitro, trifluoromethoxy, —$COOR^5$ where $R^5$ is an alkyl group, —$COR^6$, —$CONR^6R^7$ or —$NR^6R^7$ where $R^6$ and $R^7$ are each hydrogen or $C_{1-4}$ alkyl;

$R^2$ is phenyl, naphthyl or heteroaryl selected from thienyl, pyridyl, benzothienyl, quinolinyl, benzofuranyl or benzimidazolyl, said phenyl, naphthyl and heteroaryl groups being optionally substituted, or $R^2$ is furanyl optionally substituted with $C_{1-4}$ alkyl;

$R^3$ is nitrile, carboxy, —$COOR^8$ where $R^8$ is an alkyl group, or —$CONR^9R^{10}$ where $R^9$ and $R^{10}$ are each hydrogen or $C_{1-4}$ alkyl; and $R^4$ is —$NR^{11}R^{12}$, —$NR^{11}COR^{12}$, —$N(COR^{11})_2$ or —$N=CHOCH_2R^{11}$ where $R^{11}$ and $R^{12}$ are each hydrogen or $C_{1-4}$ alkyl optionally substituted with carboxy, —$N=CH-NR^{13}R^{14}$ where $R^{13}$ is hydrogen or $C_{1-4}$ alkyl and $R^{14}$ is $C_{1-4}$ alkyl, optionally substituted phenyl or optionally substituted heteroaryl,

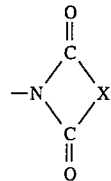

where X is $C_{2-4}$ alkylene, or —$NHSO_2R^{15}$ where R is $C_{1-4}$ alkyl, trifluoromethyl or optionally substituted phenyl;

and salts thereof. Such compounds are useful as pharmaceuticals.

With the exception of a small number of compounds, the above compounds are novel. Thus the invention also includes novel compounds of formula (I) above, provided that (i) when n is 0, $R^3$ is nitrile and $R^4$ is —$NH_2$, $R^2$ is not phenyl or phenyl substituted with 4-nitro, 2- or 4-chloro, 2,4-dichloro-, 4-nitrile, 4-methylthio, 2-bromo, 2- or 4-methyl or 2- or 4-methoxy;

(ii) when n is 0, $R^3$ is —$COOR^8$, $R^8$ is methyl or ethyl and $R^4$ is —$NH_2$, $R^2$ is not phenyl; and (iii) when n is 0, $R^3$ is —$CONH_2$ and $R^4$ is —$NH_2$, $R^2$ is not phenyl or 4-methoxyphenyl.

The compounds of the invention have been found to be active in tests which show their potential for treatment of immune diseases and diseases in which excess cell proliferation or enzyme release play a significant role.

In the above formula (I), halo is, for example, fluoro, chloro or bromo and is especially chloro. A $C_{1-4}$ alkyl group includes, for example, methyl, ethyl, propyl and butyl, and is preferably methyl or ethyl. A $C_{1-4}$ alkoxy group is one such alkyl group linked through oxygen to an aryl nucleus, and a $C_{1-4}$ alkylthio is an alkyl group linked through sulphur. A hydroxyalkyl and hydroxyalkoxy are preferably of the formula $HO(CH_2)_x$— and $HO(CH_2)_xO$—, respectively, where x is 1 to 4.

A substituted phenyl group is substituted with one or more, preferably one or two substituents each selected from halo, trifluoromethyl, $C_{1-4}$ alkoxy, hydroxy, nitro, $C_{1-4}$ alkyl, $C_{1-4}$ alkylthio, hydroxy-$C_{1-4}$ alkyl, hydroxy-$C_{1-4}$ alkoxy, trifluoromethoxy, carboxy, —$COOR^{16}$ where $R^{16}$ is an alkyl group, —$CONR^{17}R^{18}$ or —$NR^{17}R^{18}$ where $R^{17}$ and $R^{18}$ are each hydrogen or $C_{1-4}$ alkyl. When $R^{16}$ is an alkyl group it is preferably $C_{1-4}$ alkyl, especially methyl or ethyl. Substituted naphthyl and heteroaryl groups may be similarly substituted. In addition substituted phenyl includes a phenyl group in which neighbouring atoms are substituted by —$O(CH_2)_mO$—, where m is 1, 2 or 3.

When n is 1 or 2 and there are one or two substituents on the dihydronaphtho nucleus they can be at any of the positions 7 to 10, and when there are two substituents they can be the same or different. It is preferred that the dihydronaphtho nucleus is unsubstituted or that it bears a single substituent at the 9-position.

When $R^1$ is —$COOR^5$, $R^5$ can be any alkyl group and is preferably $C_{1-4}$ alkyl, especially methyl or ethyl.

When $R^1$ is a nitrogen-containing heterocycle it is preferably selected from 2-pyridyl, 3-pyridyl, 4-pyridyl, 1-piperidino, 1-pyrrolidino and 4-morpholinyl.

When $R^2$ is heteroaryl it is preferably 2-thienyl, 3-thienyl, 2-pyridyl, 3-pyridyl, 4-pyridyl, 2-benzothienyl, 3-benzothienyl, 2-quinolinyl, 3-quinolinyl, 2-benzofuranyl, 3-benzofuranyl, 2-benzidimazolyl, 2-furanyl or 3-furanyl. A naphthyl group is attached at the 1- or 2- position. Such groups can be substituted at any of the available positions, but are preferably unsubstituted. Preferred values of $R^2$ are 2-thienyl, 3-thienyl, 3-pyridyl, 4-pyridyl, phenyl or substituted phenyl.

A particularly preferred value of $R^2$ is optionally substituted phenyl, preferably phenyl with a single substituent, especially nitro or trifluoromethyl.

The group $R^3$ is preferably nitrile. When $R^3$ is —$COOR^8$, $R^8$ can be any alkyl group and is preferably $C_{1-4}$ alkyl, especially methyl or ethyl.

The group $R^4$ is preferably $-NR^{11}R^{12}$, $-NR^{11}COR^{12}$ or $-N(COR^{11})_2$ where $R^{11}$ and $R^{12}$ are each hydrogen or $C_{1-4}$ alkyl,

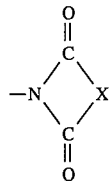

or $-NHSO_2R^{15}$.

$R^4$ is most preferably $-NR^{11}R^{12}$, for example, $-NH_2$. When $R^4$ is $-NR^{11}R^{12}$, $R^3$ is preferably nitrile, carboxy or $-CONR^9R^{10}$, and especially nitrile or $-CONR^9R^{10}$.

A particular group of compounds according to formula (I) are compounds in which n is 0, 1 or 2 and $R^1$ is attached at any of the positions 7, 8, 9 or 10, and each $R^1$ is selected from halo, amino, carboxy, trifluoromethyl, hydroxy, $C_{1-4}$ alkyl, $C_{1-4}$ alkoxy, $C_{1-4}$ alkylthio, hydroxy-$C_{1-4}$ alkyl, hydroxy-$C_{1-4}$ alkoxy or nitrogen-containing heterocyclyl;

$R^2$ is phenyl, naphthyl or heteroaryl selected from thienyl, pyridyl, benzothienyl, quinolinyl, benzofuranyl or benzimidazolyl, said phenyl, naphthyl and heteroaryl groups being optionally substituted with one or two substituents each selected from nitro, trifluoromethyl, halo, $C_{1-4}$ alkyl, $C_{1-4}$ alkoxy, carboxy, or $-O-(CH_2)_x-O-$ where x is 1 to 4, or $R^2$ is furanyl optionally substituted with $C_{1-4}$ alkyl;

$R^3$ is nitrile, carboxy, $-COOR^8$ where $R^8$ is an alkyl group, or $-CONR^9R^{10}$ where $R^9$ and $R^{10}$ are each hydrogen or $C_{1-4}$ alkyl; and $R^4$ is $-NR^{11}R^{12}$, $-NR^{11}COR^{12}$ or $-N(COR^{11})_2$ where $R^{11}$ and $R^{12}$ are each hydrogen or $C_{1-4}$ alkyl, $-N=CHOR^{11}$ where $R^{11}$ is $C_{1-4}$ alkyl, or $-NHSO_2R^{15}$ where $R^{15}$ is $C_{1-4}$ alkyl, trifluoromethyl or phenyl optionally substituted with one to three substituents each selected from $C_{1-4}$ alkyl, $C_{1-4}$ alkoxy, nitro, halo and trifluoromethyl; provided that when n is 0, $R^3$ is $-CONH_2$ or $-COOR^8$ and $R^4$ is $-NH_2$, $R^2$ is not phenyl or 4-methoxyphenyl, and provided that when n is 0, $R^3$ is nitrile and $R^4$ is $-NH_2$, $R^2$ is not phenyl or phenyl substituted with 4-nitro, 2- or 4-chloro, 2,4-dichloro-, 2-bromo, 2- or 4-methyl or 2- or 4-methoxy;

and salts thereof.

A preferred group of compounds for use in the present invention is of the formula (II):

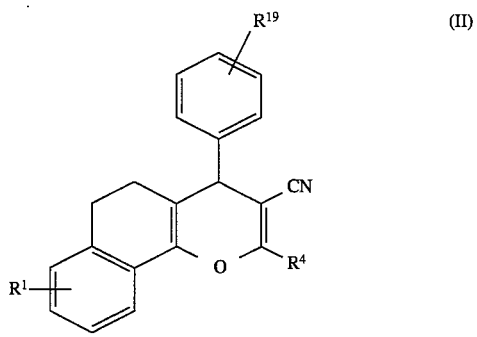

(II)

in which $R^1$ is hydrogen, $C_{1-4}$ alkoxy, halo, hydroxy, carboxy, trifluoromethyl or trifluoromethoxy, $R^4$ is $-NH_2$, $-NR^{11}COR^{12}$ or $-N(COR^{12})_2$ where $R^{11}$ is hydrogen or $C_{1-4}$ alkyl and $R^{12}$ is $C_{1-4}$ alkyl, or

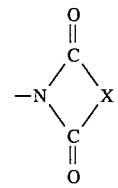

where X is $C_{1-4}$ alkyene, and $R^{19}$ is nitro, trifluoromethyl, halo, $C_{1-4}$ alkoxy, trifluoromethoxy, carboxy or $-COOR^{16}$ where $R^{16}$ is an alkyl group. It is frequently preferred that the substituent group $R^{19}$ is in the 3-position.

A further preferred group of compounds is of formula (II) above, in which $R^1$ is hydrogen, $C_{1-4}$ alkoxy or halo, $R^4$ is $-NH_2$ and $R^{19}$ is nitro or trifluoromethyl. The $R^1$ group is preferably attached at the 9-position, and the $R^{19}$ group at the 3-position.

It will be appreciated that when, for example, $R^1$ or $R^3$ is carboxy or $R^2$ is phenyl substituted by carboxy, an opportunity exists for salts to be formed. They can be derived from any of the well known bases. Examples of base salts are those derived from ammonium hydroxide and alkali and alkaline earth metal hydroxides, carbonates and bicarbonates, as well as salts derived from aliphatic and aromatic amines, aliphatic diamines and hydroxy alkylamines. Bases especially useful in the preparation of such salts include ammonium hydroxide, potassium carbonate, sodium bicarbonate, lithium hydroxide, calcium hydroxide, methylamine, diethylamine, ethylene diamine, cyclohexylamine and ethanolamine. The potassium, sodium and lithium salt forms are particularly preferred.

In addition to pharmaceutically-acceptable salts, other salts are included in the invention. They may serve as intermediates in the purification of compounds or in the preparation of other, for example pharmaceutically-acceptable, acid addition salts, or are useful for identification, charaterisation or purification.

In addition to salts formed with carboxy groups there can, of course, be esters formed with these same groups. Preferred esters are those derived from alcohols and especially $C_{1-4}$ alcohols such as, for example, the methyl or ethyl esters.

It will be appreciated that the compounds of the invention contain an asymmetric carbon atom which gives rise to enantiomers. The compounds are normally prepared as racemates and can conveniently be used as such, but individual enantiomers can be isolated by conventional techniques if so desired. Such racemates and individual enantiomers form part of the present invention.

The invention also comprises a process for producing a compound of the formula (I) above, which comprises:

(1) reacting a compound of the formula (III):

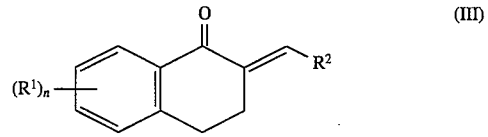

(III)

with malononitrile to give a compound of formula (I) in which $R^3$ is nitrile and $R^4$ is $-NH_2$, (2) converting a compound of the formula (IV):

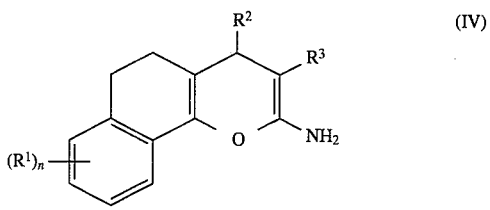

to a compound of formula (I) in which $R^4$ is $-NR^{11}R^{12}$, $-NR^{11}COR^{12}$, $-N(COR^{11})_2$, $-N=CHOCH_2R^{11}$, $-N=CHR^{13}R^{14}$, $-N=CH-NR^{13}R^{14}$,

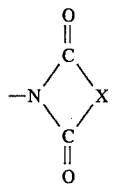

or $-NHSO_2R^{15}$, or (3) converting a compound of the formula (V):

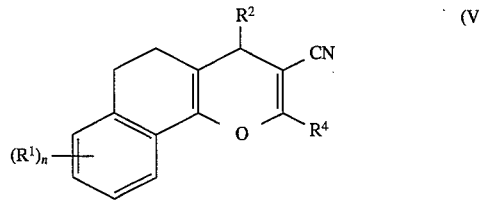

in which $R^4$ is $-NR^{11}COR^{12}$ or $-N(COR^{11})_2$ to a compound of formula (I) in which $R^3$ is carboxy, $-COOR^8$ or $-CONR^9R^{10}$.

With regard to process (1), the reaction is preferably carried out at a temperature of from 0° C. to 100° C. and in the presence of an organic solvent, such as for example ethanol. Compounds of formula (III) are known or can be easily synthesised by known methods. For example, they can be prepared from compounds of formula:

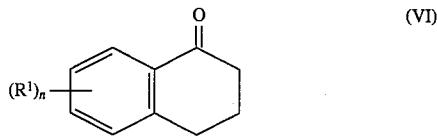

by reaction with an aldehyde of formula $R^2CHO$ in the presence of an acid catalyst such as, for example, toluene sulphonic acid, or when $R^2$ is an acid sensitive group such as pyridyl, under basic conditions, with, for example, potassium hydroxide and ethanol.

With regard to process (2), the free enamine can be prepared by reaction (1) and subsequently converted to compounds in which $R^4$ takes other values. For example, the free amino group can be alkylated with reagents of formula $R^{11}X$ or $R^{12}X$ where X is halogen, to give the mono- or di-alkylated product. Similarly the amino group can be acylated with an acylating reagent of formula $R^{11}COX$ or $(R^{11}CO)_2O$ to give compounds in which $R^4$ is $-NR^{11}COR^{12}$ or $-N(COR^{11})_2$. Compounds in which $R^4$ is $-N=CHOCH_2R^{11}$ are prepared by reaction with the appropriate trialkyl orthoformate, and those in which $R^4$ is $-NHSO_2R^{15}$ by reaction with a sulphonyl halide of formula $R^{15}SO_2X$. Compounds in which $R^4$ is $-N=CH-NR^{13}R^{14}$ can be made by reacting a compound in which $R^4$ is $-N=CHOCH_2R^{11}$ with the appropriate amine.

With regard to process (3), compounds of formula (V) can be converted to those in which $R^3$ is carboxy, $-COOR^8$ or $-CONR^9R^{10}$ by conventional means. For example, the nitrile group is readily hydrolysed to carboxy which, in turn, can be esterified to give $-COOR^8$, or reacted with amine to yield $-CONR^9R^{10}$.

Compounds of the formula (V) can be prepared by acylation of compounds derived by process (1). Compounds in which $R^4$ is other than $-NR^{11}COR^{12}$ and $-N(COR^{11})_2$ can be prepared from the product of process 3 by removal of the acyl group or groups and subsequent reaction of the amino compound thus produced, with appropriate reagents.

As mentioned above, the compounds have pharmaceutical activity. They have an antiproliferative effect on cell division, and are thus indicated for use in the treatment of diseases where excess cell proliferation or enzyme release is an important aspect of the pathology.

For example, the compounds of the invention inhibit the natural proliferation of 3T3 fibroblasts at $IC_{50}$ concentrations of below 20μ molar.

Furthermore, the compounds have been shown to modify the immune response by inhibiting concanavalin A-induced T-cell proliferation in the test described by Lacombe P. et al., FEBS, 3048, 191, 227–230. In general the compounds of the invention have an $IC_{50}$ value in this test of below 10 μM.

The compounds also inhibit cell proliferation in an NS-1 murine B-lymphoma line, and phorbol ester-stimulated plasminogen activator synthesis in bovine retinal capillary endothelial cells.

Inhibition of macrophage-conditioned medium induced neutral protease release in chondrocytes has also been observed in the test described by K. Deshmukh-Phadke, M. Lawrence and S. Nanda, Biochem. Biophys. Res. Commun., 1978, 85, 490–496.

Such properties show that the compounds have potential in the treatment of a wide range of diseases such as, for example, rheumatoid arthritis, otherosclerosis, cirrhosis, fibrosis and cancer, and for the treatment of auto-immune diseases such as, for example, systemic lupus, and in the prevention of graft rejection. They are also indicated for the treatment of asteoarthritis and diabetic complications.

Furthermore, compounds of the invention have been shown to inhibit vascular smooth cell proliferation. This has been demonstrated by using cultured smooth cells derived from rabbit aortae, proliferation being determined by the measurement of DNA synthesis. Cells are obtained by explant method as described in Ross, J. of Cell Bio. 50: 172 (1971). Cells are plated in 96 well microtiter plates for five days. The cultures become confluent and growth arrested. The cells are then transferred to Dulbecco's Modified Eagle's Medium (DMEM) containing 0.5-2% platelet poor plasma, 2 mM L-glutamine, 100 U/ml penicillin, 100 μg ml streptomycin, 1 μC/ml $^3$H-thymidine, 20 ng/ml platelet-derived growth factor and varying concentrations of the compounds. Stock solution of compounds is prepared in dimethyl sulphoxide and then diluted to appropriate concentration (0.01–10 μg/ml) in the above assay medium. Cells are then incubated at 37° C. for 24 hours under 5% $CO_2$/95% air. At the end of 24 hours, the cells are fixed in methanol. $^3$H thymidine incorporation in DNA was then determined by scintillation counting as described in Bonin et al., Exp. Cell Res. 181: 475–482 (1989).

Inhibition of smooth muscle cell proliferation by the compounds of the invention is further demonstrated by determining their effects on exponentially growing cells. Smooth muscle cells from rabbit aortae are seeded in 12 well tissue culture plates in DMEM containing 10% fetal bovine serum, 2 mM L-glutamine, 100 U/ml penicillin, and 100 µg/ml streptomycin. After 24 hours, the cells are attached, the medium is replaced with DMEM containing 2% platelet poor plasma, 2 mM L-glutamine, 100 U/ml penicillin, 100 µg/ml streptomycin, 40 ng/ml platelet-derived growth factor and indicated concentrations of the compounds. Cells are allowed to grow for four days. Cells are treated with trypsin and number of cells in each cultures is determined by counting using a ZM-Coulter counter.

Activity in the above tests indicates that the compounds of the invention are of potential in the treatment of restenosis, which is characterised by the migration and proliferation of smooth muscle cells in response to injury. Thus the invention specifically provides a method of treating restenosis, which comprises administering to a patient in need of treatment a therapeutic dosage of a compound of the formula (I).

The invention also includes a pharmaceutical composition comprising a pharmaceutically-acceptable diluent or carrier in association with a compound of formula (I), or a pharmaceutically-acceptable salt thereof.

The compounds may be administered by various routes, for example, by the oral or rectal route, topically or parenterally, for example by injection, being usually employed in the form of a pharmaceutical composition. Such compositions form part of the present invention and are prepared in a manner well known in the pharmaceutical art and normally comprise at least one active compound in association with a pharmaceutically-acceptable diluent or carrier. In making the compositions of the present invention, the active ingredient will usually be mixed with a carrier, or diluted by a carrier, and/or enclosed with a carrier which may, for example, be in the form of a capsule, sachet, paper or other container. Where the carrier serves as a diluent, it may be solid, semi-solid, or liquid material which acts as a vehicle, excipient or medium for the active ingredient. Thus, the composition may be in the form of tablets, lozenges, sachets, cachets, elixirs, suspensions, as a solid or in a liquid medium, ointments containing, for example, up to 10% by weight of the active compound, soft and hard gelatin capsules, suppositories, injection solutions and suspensions and sterile packaged powders.

Some examples of suitable carriers are lactose, dextrose, sucrose, sorbitol, mannitol, starches, gum acacia, calcium phosphate, alginates, tragacanth, gelatin, syrup, methyl cellulose, methyl- and propyl- hydroxybenzoate, talc magnesium stearate and mineral oil. The compositions of the injection may, as it well known in the art, be formulated so as to provide quick, sustained or delayed release of the active ingredient after administration to the patient.

When the compositions are formulated in unit dosage form, it is preferred that each unit dosage form contains from 5 mg to 500 mg, for example, from 25 mg to 200 mg. The term 'unit dosage form' refers to physically discrete units suitable as unit dosages for human subjects and animals, each unit containing a predetermined quantity of active material calculated to produce the desired therapeutic effect, in association with the required pharmaceutical carrier.

The active compounds are effective over a wide dosage range and, for example, dosages per day will normally fall within the range of from 0.5 to 300 mg/kg, more usually in the range of from 5 to 100 mg/kg. However, it will be understood that the amount administered will be determined by the physician in the light of the relevant circumstances, including the condition to be treated, the choice of compound to be administered and the chosen route of administration, and therefore the above dosage ranges are not intended to limit the scope of the invention in any way.

In the treatment of restenosis, the administration of a compound of the invention may be local or systemic delivery. Systemic delivery includes techniques that introduce the compound to the entire organism. Examples of systemic delivery include oral and intravenous administration.

The local delivery of a compound of the invention may be by a variety of techniques which administer the compound at or near the proliferative site. Examples of local delivery techniques are not intended to be limiting but to be illustrative of the techniques available. Examples include local delivery catheters, site specific carriers, implants, or direct injection.

Local delivery by a catheter allows the administration of a pharmaceutical agent directly to the proliferative lesion. Examples of local delivery using a balloon catheter are described in EP 0 383 492 A2 and U.S. Pat. No. 4,636,195 (Wolinsky, 13th Jan., 1987).

Local delivery by an implant describes the surgical placement of a matrix that contains the pharmaceutical agent into the proliferative lesion. The implanted matrix releases the pharmaceutical agent by diffusion, chemical reaction, or solvent activators. Langer, *Science* 249: 1527–1533 (September 1990). An example of local delivery by an implant is the use of a stent. Stents are designed to mechanically prevent the collapse and reocclusion of the coronary arteries. Incorporating a pharmaceutical agent into the stent delivers the drug directly to the proliferative site. Local delivery by this technique is described in Kohn, *Pharmaceutical Technology* (October 1990). A second example is a delivery system in which a polymer that contains the pharmaceutical agent is injected into the lesion in liquid form. The polymer then cures to form the implant in situ. This technique is described in PCT WO 90/03768 (Donn, 19th Apr. 1990). Another example is the delivery of a pharmaceutical agent by polymeric endoluminal sealing. This technique uses a catheter to apply a polymeric implant to the interior surface of the lumen. The pharmaceutical agent incorporated into the biodegradable polymer implant is thereby released at the surgical site. It is described in PCT WO 90/01969 (Schindler, 23rd Aug. 1989). A final example of local delivery by an implant is by direct injection of vesicles or microparticulates into the proliferative site. These microparticulates may be composed of substances such as proteins, lipids, carbohydrates or synthetic polymers. These microparticulates have the pharmaceutical agent incorporated throughout the microparticle or over the microparticle as a coating. Delivery systems incorporating microparticulates are described in Lange, *Science* 249: 1527–1533 (September 1990) and Mathiowitz, et al., *J. App. Poly. Sci.*, 26: 809 (1981).

Local delivery by site specific carriers describes attaching the pharmaceutical agent to a carrier which will direct or link the drug to the proliferative cells. Examples of this delivery technique include the use of carriers such as a protein ligand or a monoclonal antibody or a membrane anchored linker. Lange, *Science* 249: 1527–1533 (September 1990); Langworth, *Genetic Engineering News* (September 1990).

Local delivery by direct injection describes injecting fine particles of the compound suspended in an inert carrier such as sterile saline solution directly into the proliferative region.

The examples of local delivery are merely illustrative and are not mutually exclusive. For example, the delivery of microparticles to the proliferative smooth muscle cells may be by a local delivery catheter or direct injection.

The dosage of a compound of the invention for treatment of restenosis is dependent upon the method of administration and the particular circumstances of the patient. A therapeutic dosage is an amount sufficient to inhibit the migration and proliferation of vascular smooth muscle cells. The preferred dosage range is defined to be about 1 μg/day to about 500,000 μg/day delivered at or near the proliferative site.

The term 'treating' includes the administration of a compound of the present invention to prevent the onset of the symptoms, alleviating the symptoms, or eliminating the disease, condition, or disorder.

The invention is illustrated by the following Examples.

EXAMPLE 1

Preparation of Intermediates (1) A mixture of 3,4-dihydro-1(2H)-naphthalenone (21.9 g), 3-nitrobenzaldehyde (22.6 g) and p-toluenesulphonic acid monohydrate (50 mg) in toluene (250 ml) was stirred at reflux with separation of water for 4.5 hours. The brown solution was allowed to cool overnight. The resulting yellow-orange deposited solid was filtered off, washed well with toluene and dried in vacuo yielding 2-(3-nitrobenzylidene)-3,4-dihydro-1(2H)-naphthalenone as crisp yellow needles.

(2) A mixture of 3,4-dihydro-1(2H)-naphthalenone (4.5 g) and 4-tert-butylbenzaldehyde (5.0 g) was stirred with a solution of 4% potassium hydroxide in methanol (100 ml) for 64 hours at room temperature. The mixture was neutralised with glacial acetic acid, followed by dilution with water (100 ml). The resulting copious white precipitate was filtered off, washed with water and dried in vacuo to give 2-(4-tert-butylbenzylidene)-3,4-dihydro-1(2H)-naphthalenone.

The following compounds were prepared by methods similar to the above:
2-(4-Bromobenzylidene)-3,4-dihydro-1(2H)-naphthalenone
2-(4-Chlorobenzylidene)-3,4-dihydro-1(2H)-naphthalenone
2-(4-Fluorobenzylidene)-3,4-dihydro-1(2H)-naphthalenone
2-(3,4-Dichlorobenzylidene)-3,4-dihydro-1(2H)-naphthalenone
2-(3,4-Dichlorobenzylidene)-5-methoxy-3,4-dihydro-1(2H)-naphthalenone
2-(3,4-Dichlorobenzylidene)-6-methoxy-3,4-dihydro-1(2H)-naphthalenone
2-(3,4-Dichlorobenzylidene)-7-methoxy-3,4-dihydro-1(2H)-naphthalenone
2-(4-Chloro-3-trifluoromethylbenzylidene)-3,4-dihydro-1(2H)-naphthalenone
2-(4-Methoxybenzylidene)-3,4-dihydro-1(2H)-naphthalenone
2-(3,4-Dimethoxybenzylidene)-3,4-dihydro-1(2H)-naphthalenone
2-(3,4-Methylenedioxybenzylidene)-3,4-dihydro-1(2H)-naphthalenone
7-Methoxy-2-(3,4-methylenedioxybenzylidene)-3,4-dihydro-1(2H)-naphthalenone
2-(1,4-Benzodioxan-6-ylidene)-3,4-dihydro-1(2H)-naphthalenone
2-(4-Dimethylaminobenzylidene)-3,4-dihydro-1(2H)-naphthalenone
2-(3,5-Di-tert-butyl-4-hydroxybenzylidene)-3,4-dihydro-1(2H)-naphthalenone
2-(3-Trifluoromethylbenzylidene)-3,4-dihydro-1(2H)-naphthalenone
2-(4-Trifluoromethylbenzylidene)-3,4-dihydro-1(2H)-naphthalenone
2-(4-Nitrobenzylidene)-3,4-dihydro-1(2H)-naphthalenone
5-Methoxy-2-(4-nitrobenzylidene)-3,4-dihydro-1(2H)-naphthalenone
6-Methoxy-2-(4-nitrobenzylidene)-3,4-dihydro-1(2H)-naphthalenone
7-Methoxy-2-(4-nitrobenzylidene)-3,4-dihydro-1(2H)-naphthalenone
2-(4-Methanesulphonylbenzylidene)-3,4-dihydro-1(2H)-naphthalenone
2-(4-Methanesulphonylbenzylidene)-7-methoxy-3,4-dihydro-1(2H)-naphthalenone
2-(4-Methoxycarbonylbenzylidene)-3,4-dihydro-1(2H)-naphthalenone
2-(2-Naphthylidene)-3,4-dihydro-1(2H)-naphthalenone
2-(2-Furfurylidene)-7-methoxy-3,4-dihydro-1(2H)-naphthalenone
2-(2-Thienylidene)-3,4-dihydro-1(2H)-naphthalenone
7-Methoxy-2-(2-thienylidene)-3,4-dihydro-1(2H)-naphthalenone
2-(3-Thienylidene)-3,4-dihydro-1(2H)-naphthalenone
7-Methoxy-2-(3-thienylidene)-3,4-dihydro-1(2H)-naphthalenone
7-Methoxy-2-(3-methyl-2-thienylidene)-3,4-dihydro-1(2H)-naphthalenone
7-Methoxy-2-(5-methoxy-2-thienylidene)-3,4-dihydro-1(2H)-naphthalenone
7-Methoxy-2-(1-methyl-2-pyrrolylmethylene)-3,4-dihydro-1(2H)-naphthalenone
2-(3-Pyridylmethylene)-3,4-dihydro-1(2H)-naphthalenone
7-Methoxy-2-(3-pyridylmethylene)-3,4-dihydro-1(2H)-naphthalenone
7-Methoxy-2-(4-pyridylmethylene)-3,4-dihydro-1(2H)-naphthalenone
2-(Benzo[b]thien-2-ylidene-7-methoxy-3,4-dihydro-1(2H)-naphthalenone
2-(3-Bromobenzylidene)-3,4-dihydro-1(2H)-naphthalenone
2-(3-Chlorobenzylidene)-3,4-dihydro-1(2H)-naphthalenone
2-(3-Fluorobenzylidene)-3,4-dihydro-1(2H)-naphthalenone
2-(3,4-Difluorobenzylidene)-3,4-dihydro-1(2H)-naphthalenone
2-(3-Fluoro-4-methoxybenzylidene)-3,4-dihydro-1(2H)-naphthalenone
2-(3-Chloro-4-methoxybenzylidene)-3,4-dihydro-1(2H)-napthalenone
2-(3-Chloro-4-fluorobenzylidene)-3,4-dihydro-1(2H)-naphthalenone
2-(3-Bromo-4-fluorobenzylidene)-3,4-dihydro-1(2H)-naphthalenone
2-(3-Methoxybenzylidene)-3,4-dihydro-1(2H)-naphthalenone
2-(3-Trifluoromethoxybenzylidene)-3,4-dihydro-1(2H)-naphthalenone
2-[3,5-Bis(trifluoromethyl)benzylidene]-3,4-dihydro-1(2H)-naphthalenone
2-(3-Methoxycarbonylbenzylidene)-3,4-dihydro-1(2H)-naphthalenone
7-Methoxy-2-(3-methoxycarbonylbenzylidene)-3,4-dihydro-1(2H)-naphthalenone
7-Methoxy-2-(3-nitrobenzylidene)-3,4-dihydro-1(2H)-naphthalenone To a stirred suspension of 2-(3-nitrobenzylidene)-3,4-dihydro-1(2H)-naphthalenone (29.0 g) and malononitrile (10.27 g) in dry dimethylformamide (250 ml) at room temperature was added piperidine (2 ml) dropwise. The mixture turned black and all solid dissolved. After 24 hours, the solution was poured into saturated aqueous sodium chloride solution (1 liter) whereupon a red gummy solid was deposited. The mixture was filtered and the collected gum washed with water and then stirred with methanol for 30 minutes. Filtration and drying in vacuo yielded 2-amino-4-(3-nitrophenyl)-4H-5,6-dihydronaphtho[1,2-b]pyran 3-carbonitrile as a very pale yellow powder, m.p. 175°–176° C.

EXAMPLE 3

To a stirred suspension of 2-(4-trifluoromethylbenzylidene)-3,4-dihydro-1(2H)-naphthalenone (27.0 g) and malononitrile (8.85 g) in dimethylformamide (150 ml) at room temperature was added dropwise piperidine (4 ml). The mixture turned black and all the solid dissolved over a two hour period. After 24 hours, the solution was poured into a 1:1 mixture of water and dichloromethane (1 liter). The organic layer was separated and the aqueous phase extracted further with dichloromethane (2×200 ml). The combined organics were washed with water (2×300 ml), dried (MgSO$_4$), filtered and concentrated in vacuo to yield a brown gum. This was triturated with methanol to yield a solid that was recrystallised from methanol/water yielding 2-amino-4-(4-trifluoromethylphenyl)-4H-5,6-dihydronaphtho [1,2-b]pyran 3-carbonitrile as glistening colourless crystals, m.p. 204°–206° C.

The following compounds were prepared in a manner similar to that described in Examples 2 or 3.

2-Amino-4-(4-bromophenyl)-4H-5,6-dihydronaphtho[1,2-b]pyran 3-carbonitrile, m.p. 178°–179° C.

2-Amino-4-(4-chlorophenyl)-4H-5,6-dihydronaphtho[1,2-b]pyran 3-carbonitrile, m.p. 171°–172° C.

2-Amino-4-(4-fluorophenyl)-4H-5,6-dihydronaphtho[1,2-b] pyran 3-carbonitrile, m.p. 188°–190° C.

2-Amino-4-(3,4-dichlorophenyl)-4H-5,6-dihydronaphtho[1,2-b]pyran 3-carbonitrile, m.p. 215°–216° C.

2-Amino-4-(3,4-dichlorophenyl)-7-methoxy-4H-5,6-dihydronaphtho[1,2-b]pyran 3-carbonitrile, m.p. 216°–217° C.

2-Amino-4-(3,4-dichlorophenyl)-8-methoxy-4H-5,6-dihydronaphtho[1,2-b]pyran 3-carbonitrile, m.p. 199°–200° C.

2-Amino-4 -(3,4-dichlorophenyl)-9-methoxy-4H-5,6-dihydronaphtho[1,2-b]pyran 3-carbonitrile, m.p. 200°–201° C.

2-Amino-4 -(4-chloro-3-trifluoromethylphenyl)-4H-5,6 -dihydronaphtho[1,2b]pyran 3-carbonitrile, m.p. 204°–206° C.

2-Amino-4-(4-methoxyphenyl)-4H-5,6-dihydronaphtho[1,2-b]pyran 3-carbonitrile, m.p. 177°–178° C.

2-Amino-4-(3,4-dimethoxyphenyl)-4H-5,6-dihydronaphtho [1,2-b]pyran 3-carbonitrile, m.p. 190°–191° C.

2-Amino-4-(3,4-methylenedioxyphenyl)-4H-5,6-dihydronaphtho[1,2-b]pyran 3-carbonitrile, m.p. 250°–252° C.

2-Amino-9-methoxy-4-(3,4-methylenedioxyphenyl)-4H-5,6-dihydronaphtho[1,2-b]pyran 3-carbonitrile, m.p. 185°–186° C.

2-Amino-4-(1,4-benzodioxan-6-yl)-4H-5,6-dihydronaphtho [1,2-b]pyran 3-carbonitrile, m.p. 203°–204° C.

2-Amino-4-(4-dimethylaminophenyl)-4H-5, 6-dihydronaphtho[1,2-b]pyran 3-carbonitrile, m.p. 201°–202° C.

2-Amino-4- (3,5-di-tert-butyl-4-hydroxyphenyl)-4H-5,6-dihydronaphtho[1,2-b]pyran 3-carbonitrile, m.p. 222°–224° C.

2-Amino-4-(4-tert-butylphenyl)-4H-5,6-dihydronaphtho[1,2-b]pyran 3-carbonitrile, m.p. 194°–195° C.

2-Amino-4-(3-trifluoromethylphenyl)-4H-5,6-dihydronaphtho[1,2-b]pyran 3-carbonitrile, m.p. 195.5°–196° C.

2-Amino-4-(4-nitrophenyl)-4H-5,6-dihydronaphtho[1,2-b] pyran 3-carbonitrile, m.p. 213°–214° C.

2-Amino-7-methoxy-4-(4-nitrophenyl)-4H-5,6-dihydronaphtho[1,2-b]pyran 3-carbonitrile, m.p. 194°–195° C.

2-Amino-8-methoxy-4-(4-nitrophenyl)-4H-5,6-dihydronaphtho[1,2-b]pyran 3-carbonitrile, m.p. 166°–167° C.

2-Amino-9-methoxy-4-(4-nitrophenyl)-4H-5,6-dihydronaphtho[1,2-b]pyran 3-carbonitrile, m.p. 185°–186° C.

2-Amino-4-(4-methanesulphonylphenyl)-4H-5,6-dihydronaphtho[1,2-b]pyran 3-carbonitrile, m.p. 196°–197° C.

2-Amino-4-(4-methanesulphonylphenyl)-9-methoxy-4H-5, 6-dihydronaphtho[1,2-b]pyran 3-carbonitrile, m.p. 188°–189° C.

Methyl-4-(2-Amino-3-cyano-4H-5,6-dihydronaphtho[1,2-b]pyran-4-yl) benzoate, m.p. 189°–190° C.

2-Amino-4-(2-naphthyl)-4H-5,6-dihydronaphtho[1,2-b]pyran 3-carbonitrile, m.p. 185°–186° C.

2-Amino-4-(2-furyl)-9-methoxy-4H-5,6-dihydronaphtho[1, 2-b]pyran 3-carbonitrile, m.p. 148°–149° C.

2-Amino-4-(2-thienyl)-4H-5,6-dihydronaphtho[1,2-b]pyran 3-carbonitrile, m.p. 170°–171° C.

2-Amino-4-(3-thienyl)-4H-5,6-dihydronaphtho[1,2-b]pyran 3-carbonitrile, m.p. 158°–159° C.

2-Amino-9-methoxy-4-(2-thienyl)-4H-5,6-dihydronaphtho [1,2-b]pyran 3-carbonitrile, m.p. 198°–199° C.

2-Amino-9-methoxy-4-(3-thienyl)-4H-5,6-dihydronaphtho [1,2-b]pyran 3-carbonitrile, m.p. 160°–161° C.

2-Amino-9-methoxy-4-(3-methyl 2-thienyl)-4H-5,6-dihydronaphtho[1,2-b]pyran 3-carbonitrile, m.p. 179°–180° C.

2-Amino-9-methoxy-4-(5-methoxy 2-thienyl)-4H-5,6-dihydronaphtho[1,2-b]pyran 3-carbonitrile, m.p. 130°–131° C.

2-Amino-9-methoxy-4-(1-methyl 2-pyrrolyl)-4H-5,6-dihydronaphtho[1,2-b]pyran 3-carbonitrile, m.p. 190°–191° C.

2-Amino-4-(3-pyridyl)-4H-5,6-dihydronaphtho[1,2-b]pyran 3-carbonitrile, m.p. 165°–166° C.

2-Amino-9-methoxy-4-(3 -pyridyl)-4H-5,6-dihydronaphtho [1,2-b]pyran 3-carbonitrile, m.p. 230°–232° C.

2-Amino-9-methoxy-4-(4-pyridyl)-4H-5,6-dihydronaphtho [1,2-b]pyran 3-carbonitrile, m.p. 205°–207° C.

2-Amino-4-(benzo[b]thiophen-2-yl)-9-methoxy-4H-5,6-dihydronaphtho[1,2-b]pyran 3-carbonitrile, m.p. 214°–215° C.

2-Amino-4-(3-bromophenyl)-4H-5,6-dihydronaphtho[1,2-b]pyran 3-carbonitrile, m.p. 176°–177° C.

2-Amino-4-(3-chlorophenyl)-4H-5,6-dihydronaphtho[1,2-b]pyran 3-carbonitrile, m.p. 175°–176° C.

2-Amino-4-(3-fluorophenyl)-4H-5,6-dihydronaphtho[1,2 -b]pyran 3-carbonitrile, m.p. 169°–170° C.

2-Amino-4-(3,4-difluorophenyl)-4H-5,6-dihydronaphtho[1, 2-b]pyran 3-carbonitrile, m.p. 168°–170° C. 2-Amino-4-(3-fluoro-4-methoxyphenyl)-4H-5,6-dihydronaphtho[1, 2-b]pyran 3-carbonitrile, m.p. 219°–222° C.

2-Amino-4-(3-chloro-4-methoxyphenyl)-4H-5,6-dihydronaphtho[1,2-b]pyran 3-carbonitrile, m.p. 203° C.

2-Amino-4-(3-chloro-4-fluorophenyl)-4H-5,6-dihydronaphtho[1,2-b]pyran 3-carbonitrile, m.p. 184°–185° C.

2-Amino-4-(3-bromo-4-fluorophenyl)-4H-5,6-dihydronaphtho[1,2-b]pyran 3-carbonitrile, m.p. 185°–187° C.

2-Amino-4-(3-methoxyphenyl)-4H-5,6-dihydronaphtho[1,2-b]pyran 3-carbonitrile, m.p. 204°–206° C.

2-Amino-4-(3-trifluoromethoxyphenyl)-4H-5,6-dihydronaphtho[1,2-b]pyran 3-carbonitrile, m.p. 141°–143° C.

2-Amino-4-[3,5-bis(trifluoromethyl)phenyl]-4H-5,6-dihydronaphtho[1,2-b]pyran 3-carbonitrile, m.p. 228°–231° C.

2-Amino-9-methoxy-4-(3-nitrophenyl)-4H-5,6-dihydronaphtho[1,2-b]pyran 3-carbonitrile, m.p. 192°–194° C.

Methyl 3-(2-amino-3-cyano-4H-5,6-dihydronaphtho[1,2-b]pyran-4-yl) benzoate, m.p. 217°–218° C.

Methyl 3-(2-amino-3-cyano-9-methoxy-4H-5,6-dihydronaphtho[1,2-b]pyran-4-yl) benzoate, m.p. 159°–160° C.

EXAMPLE 4

To a stirred ice-cooled solution of 2-amino-4-(3-nitrophenyl)-4H-5,6-dihydronaphtho [1,2-b]pyran 3-carbonitrile (12.05 g) and dry pyridine (18 ml) in dry dimethylformamide (200 ml) was added dropwise over 15 minutes acetyl chloride (16 ml). A heavy white precipitate appeared. The ice bath was removed and the mixture stirred at room temperature for 65 hours during which time all the solid dissolved and the solution had turned black. This was poured into saturated aqueous sodium chloride solution (300 ml) and the product extracted with dichloromethane (2×250 ml). The combined extracts were washed with saturated aqueous copper sulphate solution (4×200 ml), water (2×200 ml), saturated aqueous sodium chloride solution (2×200 ml) and dried (MgSO$_4$). Filtration followed by concentration in vacuo yielded a viscous red gum (16.5 g). This was dissolved in dichloromethane and passed through a pad of neutral alumina eluting with ether/dichloromethane (1:1). Combination and concentration of appropriate fractions yielded a crisp yellow solid (12.0 g). This was redissolved in dichloromethane (100 ml) and stirred with neutral alumina (50 g) for 16 hours. The alumina was filtered off, washed well with dichloromethane and the resulting solution concentrated yielding a crisp bright yellow solid (9.64 g) that was recrystallised from methanol yielding 2-acetylamino-4-(3-nitrophenyl)-4H-5,6-dihydronaphtho[1,2-b]pyran 3-carbonitrile as a pale yellow powdery solid, m.p. 219°–221° C.

The following compounds were prepared in a similar manner:

2-Acetylamino-4-(4-nitrophenyl)-4H-5,6-dihydronaphtho [1,2-b]pyran 3-carbonitrile, m.p. 231°–234° C.

2-Acetylamino-4-(3-trifluoromethylphenyl)-4H-5,6-dihydronaphtho[1,2-b]pyran 3-carbonitrile, m.p. 177°–179° C.

2-Acetylamlino-4-(4-chlorophenyl)-4H-5,6-dihydronaphtho[1,2-b]pyran 3-carbonitrile, m.p. 219°–223° C.

2-Acetylamino-4-(4-fluorophenyl)-4H-5,6-dihydronaphtho [1,2-b]pyran 3-carbonitrile, m.p. 203°–208° C.

2-Acetylamino-4-(2-thienyl)-4H-5,6-dihydronaphtho[1,2-b]pyran 3-carbonitrile, m.p. 235°–237° C.

2-Acetylamino-9-methoxy-4-(3-thienyl)-4H-5,6-dihydronaphtho[1,2-b]pyran 3-carbonitrile, m.p. 197°–198° C.

2-Acetylamlino-4-(3,4-dimethoxyphenyl)-4H-5,6-dihydronaphtho[1,2-b]pyran 3-carbonitrile, m.p. 178°–180° C.

2-Acetylamino-4-(3,4-dichlorophenyl)-4H-5,6-dihydronaphtho[1,2-b]pyran 3-carbonitrile, m.p. 196°–198° C.

2-Acetylamino-4-(3-pyridyl)-4H-5,6-dihydronaphtho[1,2-b]pyran 3-carbonitrile, m.p. 205°–207° C.

2-Acetylamino-9-methoxy-4-(2-thienyl)-4H-5,6 -dihydronaphtho[1,2-b]pyran 3-carbonitrile, m.p. 202°–204° C.

Methyl 3-[2-(N-acetylamino)-3-cyano-4H-5,6-dihydronaphtho[1,2-b]pyran-4-yl]benzoate, m.p. 220°–225° C.

Methyl 3-[2-(N-acetylamino)-3-cyano-9-methoxy-4H-5,6-dihydronaphtho[1,2-b]pyran-4-yl] benzoate, m.p. 90°–91° C.

EXAMPLE 5

To a stirred suspension of sodium hydride (60% dispersion in oil, 0.39 g) in dry dimethylformamide (80 ml) at –5° C. under nitrogen was added dropwise during 10 minutes a solution of 2-acetylamino-4-(3-nitrophenyl)-4H-5,6-dihydronaphtho[1,2-6]pyran 3-carbonitrile (2.80 g) in dry dimethylformamide (20 ml). The mixture rapidly turned orange and there was a weak exotherm. After stirring at –5°C. for 50 minutes, methyl iodide (1.42 g) was added dropwise. The cooling bath was removed and stirring continued at room temperature for 4 hours. The mixture was then poured into water (200 ml) and the product extracted into dichloromethane (2×100 ml). The combined organic extracts were washed with water (3×50 ml), dried (Na$_2$SO$_4$), filtered and evaporated in vacuo yielding a crisp yellow solid. This was dissolved in dichloromethane and passed through a short column of neutral alumina eluting with dichloromethane/ether (1:1). Combination and evaporation in vacuo of appropriate fractions yielded 2-(N-acetyl-N -methylamino)-4-(3-nitrophenyl)-4H-5,6-dihydronaphtho[1,2-b]pyran 3-carbonitrile as a pale yellow powder, m.p. 154°–155° C.

The following compounds were prepared in a similar manner:

2-(N-acetyl-N-methylamino)-9-methoxy-4-(3-thienyl)-4H-5,6-dihydronaphtho[1,2-b]pyran 3-carbonitrile, m.p. 181°–182° C.

Methyl 3-[2-(N-acetyl-N-methylamino)-3-cyano-4H-5,6dihydronaphtho[1,2-b]pyran-4-yl]benzoate, m.p. 137°–138° C.

Methyl 3-[2-N-acetyl-N-methylamino)-3-cyano-9-methoxy-4H-5,6-dihydronaphtho[1,2-b]pyran-4-yl]benzoate, m.p. 140°–141° C.

EXAMPLE 6

A mixture of 2-amino-4-(3-nitrophenyl)-4H-5,6-dihydronaphtho[1,2-b]pyran 3-carbonitrile (2.50 g) and triethyl orthoformate (25 ml) was heated under reflux for six hours. The cooled solution was concentrated in vacuo and the residual yellow/brown solid stirred with methanol for 30 minutes. Undissolved solid was filtered off, taken up in chloroform, chromatographed on silica gel with chloroform as eluant yielding 1.6 g of crude product. This recrystallised from ethanol yielding 2-(E)-(ethoxymethyleneamino)-4-(3-nitrophenyl)-4H-5,6-dihydronaphtho[1,2-b]pyran-3-carbonitrile as glistening pale yellow needles, m.p. 168°–171° C.

The following compounds were prepared in a similar manner:

4-(3,4-Dimethoxyphenyl)-2-(E)-ethoxymethyleneamino-4H-5,6-dihydronaphtho[1,2-b]pyran 3-carbonitrile, m.p. 86°–88° C.

-(E)-Ethoxymethyleneamino-9-methoxy-4-(2-thienyl)-4H-5,6-dihydronaphtho[1,2-b]pyran 3-carbonitrile, m.p. 132°–134° C.

4-(3,4-Dichlorophenyl)-2-(E)-ethoxymethyleneamino-4H-5,6-dihydronaphtho[1,2-b]pyran 3-carbonitrile, m.p. 156°–158° C.

2-(E)-Ethoxymethyleneamino-4-(3-pyridyl)-4H-5,6-dihydronaphtho[1,2-b]pyran 3-carbonitrile, m.p. 130°–132° C.

EXAMPLE 7

2-Amino-9-methoxy-4-(2-thienyl)-4H-5,6-dihydronaphtho[1,2-b]pyran 3-carbonitrile (0.5 g) was dissolved in tetrahydrofuran (20 ml) and treated with pyridine (0.47 g) and then succinyl chloride (0.69 g), generating a cream suspension. This was brought to reflux. After a few hours, more pyridine (0.23 g) was added. After 12 hours at reflux, the reaction mixture was allowed to cool and quenched with water. This mixture was diluted with chloroform and the two phase mixture passed through a pad of celite. The chloroform layer was separated, washed with brine and dried (MgSO$_4$). This solution was passed quickly through a small pad of silica and the resulting solution concentrated. Trituration of the residue with ethyl acetate plus a little hexane yielded 9-methoxy-2-(N-succinimido)-4-(2-thienyl)-4H-5,6-dihydronaphtho[1,2-b]pyran 3-carbonitrile as a brown solid (m.p. 234°–236° C).

The following compounds were prepared in a similar manner:

4-(3,4-Dimethoxyphenyl)-2-(N-succinimido)-4H-5,6-dihydronaphtho[1,2-b]pyran 3-carbonitrile, m.p. 220–222° C.

4-(3,4-Dichlorophenyl)-2-(N-succinimido)-4H-5,6-dihydronaphtho[1,2-b]pyran 3-carbonitrile, m.p. 215°–217° C.

4-(3-Nitrophenyl)-2-(N-succinimido)-4H-5,6-dihydronaphtho[1,2-b]pyran 3-carbonitrile, m.p. 96°–98° C.

EXAMPLE 8

2-(E)-Ethoxymethyleneamino-4-(3-nitrophenyl)-4H-5,6-dihydronaphtho [1,2-b]pyran 3-carbonitrile (0.5 g) and 2-aminopyridine (0.23 g) were dissolved in tetrahydrofuran (20 ml) and the solution heated at reflux under nitrogen overnight. Two further equivalents of 2-aminopyridine were then added and heating continued for a further 24 hours. By this time a precipitate had formed. This was collected by filtration and washed twice with warm tetrahydrofuran, yielding 1-(2-pyridyl)-3-[4-(3-nitrophenyl)-3-cyano-4H-5,6dihydronaphtho[1,2-b]pyran-2-yl]formamidine, m.p. 223°–225° C.

EXAMPLE 9

Soft Gelatin Capsule

Each soft gelatin capsule contains:

| Active ingredient | 150 mg |
| Arachis oil | 150 mg |

After mixing together, the blend is filled into soft gelatin capsules using the appropriate equipment.

EXAMPLE 10

Hard Gelatin Capsule

Each capsule contains:

| Active ingredient | 50 mg |
| PEG 4000 | 250 mg |

The PEG 4000 is melted and mixed with the active ingredient. Whilst still molten the mixture is filled into capsule shells and allowed to cool.

EXAMPLE 11

Tablets each containing 10 mg of active ingredient are made up as follows:

| Active ingredient | 10 mg |
| Starch | 160 mg |
| Microcrystalline cellulose | 100 mg |
| Polyvinylpyrrolidone (as 10% solution in water) | 13 mg |
| Sodium carboxymethyl starch | 14 mg |
| Magnesium stearate | 3 mg |
| Total | 300 mg |

The active ingredient, starch and cellulose are mixed thoroughly. The solution of polyvinylpyrrolidone is mixed with the resultant powders and passed through a sieve. The granules so produced are dried and re-passed through a sieve. The sodium carboxymethyl starch and magnesium stearate are then added to the granules which, after mixing, are compressed in a tablet machine to yield tablets each weighing 300 mg.

EXAMPLE 12

Capsules each containing 20 mg of medicament are made as follows:

| Active ingredient | 20 mg |
| Dried starch | 178 mg |
| Magnesium stearate | 2 mg |
| Total | 200 mg |

The active ingredient, starch and magnesium stearate are passed through a sieve and filled into hard gelatin capsules in 200 mg quantities.

EXAMPLE 13

The concanavalin A response of rat spleen cells was used as a primary in vitro assay to determine the activity of the compounds of the invention. Many methods for the determination of concavalin A response are described in the literature. The method employed was similar to that described by Lacombe P. et al., FEBS 3048 191 227–230. We used 2×10$^5$ cells per culture well, and concanavalin A was employed at 1 µg/ml. 2-Mercaptoethanol was a requirement (2×10M$^{-5}$) and 0.25 µCi of tritiated thymidine was added six hours before cell harvesting.

For example, the following compounds have an IC$_{50}$ in the range of from 10 nM to 2.0 µM:

2-Amino-4-(3-fluorophenyl)-4H-5,6-dihydronaphtho[1-2-b]pyran 3-carbonitrile.

2-Amino-4-(3-chloro-4-fluorophenyl)-4H-5,6-dihydronaphtho[1,2b]pyran 3-carbonitrile.

2-Amino-4-(3-methoxyphenyl)-4H-5,6-dihydronaphtho[1,2b]pyran 3-carbonitrile.

Methyl 4-(2-amino-3-cyano-4H-5,6-dihydronaphtho[1,2-b]pyran-4-yl)benzoate.

Methyl 4-(2-amino-3-cyano-9-methoxy-4H-5,6-dihydronaphtho[1,2-b]pyran-4-yl) benzoate.

2-Amino-4-(3-nitrophenyl)-4H-5,6-dihydronaphtho[1,2-b]pyran 3-carbonitrile.

2-Amino-4-(3-trifluoromethyl phenyl)-4H-5,6-dihydronaphtho[1,2-b]pyran 3-carbonitrile.

2-Amino-4-(2-thienyl)-4H-5,6-dihydronaphtho[1,2-b]pyran 3-carbonitrile.

2-Amino-9-methoxy-4-(3-thienyl)-4H-5,6-dihydronaphtho[1,2-b]pyran 3-carbonitrile.

2-Acetylamino-4-(3-nitrophenyl)-4H-5,6-dihydronaphtho[1,2-b]pyran 3-carbonitrile.

2-(E)-Ethoxymethyleneamino-4-(3-nitrophenyl)-4H-5,6-dihydronaphtho[1,2-b]pyran 3-carbonitrile.

4-(3-Nitrophenyl)-2-(N-succinimido)-4H-5,6-dihydronaphtho[1,2-b]pyran 3-carbonitrile.

We claim:

1. A compound of the formula:

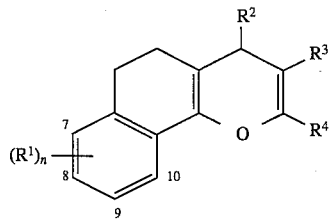

in which n is 0, 1 or 2 and $R^1$ is attached at any of the positions 7, 8, 9 or 10, and each $R^1$ is halo, carboxy, trifluoromethyl, hydroxy, $C_{1-4}$ alkyl, $C_{1-4}$ alkoxy, $C_{1-4}$ alkylthio, hydroxy-$C_{1-4}$ alkyl, hydroxy-$C_{1-4}$ alkoxy, nitrogen-containing heterocyclyl, nitro, trifluoromethoxy, —$COOR^5$ where $R^5$ is an alkyl group, —$COR^6$, —$CONR^6R^7$ or —$NR^6R^7$ where $R^6$ and $R^7$ are each hydrogen or $C_{1-4}$ alkyl;

$R^2$ is phenyl, naphthyl or heteroaryl selected from thienyl, pyridyl, benzothienyl, quinolinyl, benzofuranyl or benzimidazolyl, said phenyl, naphthyl and heteroaryl groups being optionally substituted, or $R^2$ is furanyl optionally substituted with $C_{1-4}$ alkyl;

$R^3$ is nitrile, carboxy, —$COOR^8$ where $R^8$ is an alkyl group, or —$CONR^9R^{10}$ where $R^9$ and $R^{10}$ are each hydrogen or $C_{1-4}$ alkyl; and $R^4$ is —$NR^{11}R^{12}$, —$NR^{11}COR^{12}$, —$N(COR^{11})_2$ or —$N=CHOCH_2R^{11}$ where $R^{11}$ and $R^{12}$ are each hydrogen or $C_{1-4}$ alkyl optionally substituted with carboxy, —$N=CH$—$NR^{13}R^{14}$ where $R^{13}$ is hydrogen or $C_{1-4}$ alkyl and $R^{14}$ is $C_{1-4}$ alkyl, optionally substituted phenyl or optionally substituted heteroaryl,

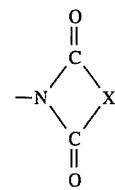

where X is $C_{2-4}$ alkylene, or —$NHSO_2R^{15}$ where $R^{15}$ is $C_{1-4}$ alkyl, trifluoromethyl or optionally substituted phenyl; provided that when n is 0, $R^3$ is nitrile and $R^4$ is —$NH_2$, $R^2$ is not phenyl or phenyl substituted with 4-nitro, 2- or 4-chloro, 2,4-dichloro-, 4-nitrile, 4-methylthio, 2-bromo, 2- or 4-methyl or 2- or 4-methoxy;

(ii) when n is 0, $R^3$ is —$COOR^8$, $R^8$ is methyl or ethyl and $R^4$ is —$NH_2$, $R^2$ is not phenyl; and (iii) when n is 0, $R^3$ is —$CONH_2$ and $R^4$ is —$NH_2$, $R^2$ is not phenyl or 4-methoxyphenyl;

and salts thereof.

2. A compound according to claim 1 in which n is 0, 1 or 2 and $R^1$ is attached at any of the positions 7, 8, 9 or 10, and each $R^1$ is selected from halo, amino, carboxy, trifluoromethyl, hydroxy, $C_{1-4}$ alkyl, $C_{1-4}$ alkoxy, $C_{1-4}$ alkylthio, hydroxy-$C_{1-4}$ alkyl, hydroxy-$C_{1-4}$ alkoxy or nitrogen-containing heterocyclyl;

$R^2$ is phenyl, naphthyl or heteroaryl selected from thienyl, pyridyl, benzothienyl, quinolinyl, benzofuranyl or benzimidazolyl, said phenyl, naphthyl and heteroaryl groups being optionally substituted with one or two substituents each selected from nitro, trifluoromethyl, halo, $C_{1-4}$ alkyl, $C_{1-4}$ alkoxy, carboxy, or —O—$(CH_2)_x$—O— where x is 1 to 4, or $R^2$ is furanyl optionally substituted with $C_{1-4}$ alkyl;

$R^3$ is nitrile, carboxy, —$COOR^8$ where $R^8$ is an alkyl group, or —$CONR^9R^{10}$ where $R^9$ and $R^{10}$ are each hydrogen or $C_{1-4}$ alkyl; and $R^4$ is —$NR^{11}R^{12}$, —$NR^{11}COR^{12}$ or —$N(COR^{11})_2$ where $R^{11}$ and $R^{12}$ are each hydrogen or $C_{1-4}$ alkyl, —$N=CHOR^{11}$ where $R^{11}$ is $C_{1-4}$ alkyl, or —$NHSO_2R^{15}$ where $R^{15}$ is $C_{1-4}$ alkyl, trifluoromethyl or phenyl optionally substituted with one to three substituents each selected from $C_{1-4}$ alkyl, $C_{1-4}$ alkoxy, nitro, halo and trifluoromethyl; provided that when n is 0, $R^3$ is —$CONH_2$ or —$COOR^8$ and $R^4$ is —$NH_2$, $R^2$ is not phenyl or 4-methoxyphenyl, and provided that when n is 0, $R^3$ is nitrile and $R^4$ is —$NH_2$, $R^2$ is not phenyl or phenyl substituted with 4-nitro, 2-or 4-chloro, 4-dichloro- ,2-bromo, 2- or 4-methyl or 2- or 4-methoxy.

3. A compound according to claim 2 in which $R^2$ is optionally substituted phenyl.

4. A compound according to claim 3 in which $R^3$ is nitrile.

5. A pharmaceutical composition comprising a compound of the formula

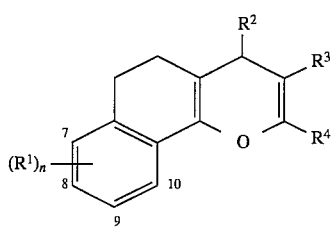

in which n is 0, 1 or 2 and $R^1$ is attached at any of the positions 7, 8, 9 or 10, and each $R^1$ is halo, carboxy, trifluoromethyl, hydroxy, $C_{1-4}$ alkyl, $C_{1-4}$ alkoxy, $C_{1-4}$ alkylthio, hydroxy-$C_{1-4}$ alkyl, hydroxy-$C_{1-4}$ alkoxy, nitrogen-containing heterocyclyl, nitro, trifluoromethoxy, —COOR$^5$ where $R^5$ is an alkyl group, —COR$^6$, —CONR$^6$R$^7$ or —NR$^6$R$^7$ where $R^6$ and $R^7$ are each hydrogen or $C_{1-}$alkyl;

$R^2$ is phenyl, naphthyl or heteroaryl selected from thienyl, pyridyl, benzothienyl, quinolinyl, benzofuranyl or benzimidazolyl, said phenyl, naphthyl and heteroaryl groups being optionally substituted, or $R^2$ is furanyl optionally substituted with $C_{1-4}$ alkyl;

$R^3$ is nitrile, carboxy, —COOR$^8$ where $R^8$ is an alkyl group, or —CONR$^9$R$^{10}$ where $R^9$ and $R^{10}$ are each hydrogen or $C_{1-4}$ alkyl; and $R^4$ is —NR$^{11}$R$^{12}$, —NR$^{11}$COR$^{12}$, —N(COR$^{11}$)$_2$ or —N=CHOCH$_2$R$^{11}$ where $R^{11}$ and $R^{12}$ are each hydrogen or $C_{1-4}$ alkyl optionally substituted with carboxy, —N=CH—NR$^{13}$R$^{14}$ where $R^{13}$ is hydrogen or $C_{1-4}$ alkyl and $R^{14}$ is $C_{1-4}$ alkyl, optionally substituted phenyl or optionally substituted heteroaryl,

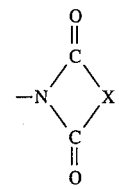

where X is $C_{2-4}$ alkylene, or —NHSO$_2$R$^{15}$ where $R^{15}$ is $C_{1-4}$ alkyl, trifluoromethyl or optionally substituted phenyl, or a pharmaceutically-acceptable salt thereof, together with a pharmaceutically-acceptable diluent or carrier therefor.

6. A pharmaceutical composition comprising a compound as defined in claim 1, or a pharmaceutically-acceptable salt thereof, together with a pharmaceutically-acceptable diluent or carrier therefor.

* * * * *

UNITED STATES PATENT AND TRADEMARK OFFICE
CERTIFICATE OF CORRECTION

PATENT NO. : 5,622,987
DATED : April 22, 1997
INVENTOR(S) : Michael Brunavs, et al.

It is certified that error appears in the above-indentified patent and that said Letters Patent is hereby corrected as shown below:

In Column 10, after line 59, insert --EXAMPLE 2--.

Signed and Sealed this

Fourth Day of August, 1998

Attest:

BRUCE LEHMAN

Attesting Officer        Commissioner of Patents and Trademarks